(12) United States Patent
Soubhie

(10) Patent No.: US 7,141,252 B2
(45) Date of Patent: Nov. 28, 2006

(54) COMPOSITION FOR THE TREATMENT OF BURNS, SUNBURNS, ABRASIONS, ULCERS AND CUTANEOUS IRRITATION

(76) Inventor: Eliana Soubhie, 67 Ted Grant Private, Ottawa, Ontario (CA) K1G 5B9

( * ) Notice: Subject to any disclaimer, the term of this patent is extended or adjusted under 35 U.S.C. 154(b) by 0 days.

(21) Appl. No.: 10/717,914

(22) Filed: Nov. 21, 2003

(65) Prior Publication Data

US 2005/0112208 A1   May 26, 2005

(51) Int. Cl.
*A61K 36/00* (2006.01)
*A61K 36/752* (2006.01)
*A61K 36/63* (2006.01)

(52) U.S. Cl. .............. 424/725; 424/775; 424/777; 424/736; 424/659; 424/520; 424/522; 424/539; 514/787

(58) Field of Classification Search ........... 424/725, 424/775, 777, 736, 659, 520, 522, 539; 514/787
See application file for complete search history.

(56) References Cited

FOREIGN PATENT DOCUMENTS

GB    2228411 A   *   8/1990

OTHER PUBLICATIONS

Lust, J. The Herb Book; Bantam Books, New York, New York (1974) p. 40.*

* cited by examiner

*Primary Examiner*—Patricia Leith
(74) *Attorney, Agent, or Firm*—Teitelbaum & MacLean; Neil Teitelbaum; Doug MacLean

(57) ABSTRACT

A topical composition and method of preparation is disclosed wherein olive oil, bees wax, lemon juice and boric acid is combined to yield a cream for application to burns. The composition makes the patient more comfortable and has been shown to promote more rapid healing with less scarring than many other products.

9 Claims, No Drawings

COMPOSITION FOR THE TREATMENT OF BURNS, SUNBURNS, ABRASIONS, ULCERS AND CUTANEOUS IRRITATION

FIELD OF THE INVENTION

The present invention concerns a composition for the treatment of burns, sunburns, abrasions, ulcers and cutaneous irritation. More specifically, the invention relates to a preparation for topical administration having analgesic, antiseptic and skin healing promoting activity. The preparation is particularly suitable for the treatment of burns, scalds and sunburns.

BACKGROUND OF THE INVENTION

As it is known, the exposure to an excessive heat of any kind causes on the human epidermis, and often also on the underlying tissues, situations of pathological alteration and lesions the seriousness of which varies according to the duration and the intensity of the exposure, and to the sensitivity of the single individual.

Real burns or scalds may be caused, for instance, by the contact with hot matter or articles, such as flames, hot liquids or burning bodies, or also by an excessive exposure to radiation sources, including the sun.

According to the current clinical classification, a burn may be of first, second or third degree, depending upon the gravity of the lesion.

The first-degree burns are limited to the superficial layers of the epidermis and are characterized by local erythema (redness) and light edema (swelling); the second-degree burns involve a damage extended to the dermis, more marked edema and formation of blisters containing serous exudate, and the third-degree burns are accompanied by a true destruction of the structural elements of the skin, with formation of blisters, sores and the presence, in the most serious cases, of charred zones. In the most critical cases the involvement is extended to general phenomena, such as shock, acute intoxication and anaemia.

In most cases, in agreement with the topical administration of severity, recourse is made to the topical administration of remedies that should exert a range of different actions, including an analgesic action, a stimulating action on the reparative processes of the skin tissues, i.e. an action promoting healing of the lesions, an anti-inflammatory action and, moreover, an antiseptic action, in order to prevent the occurrence of secondary infections on the affected zones.

Actually, the injured tissues are particularly prone to the development of infections, which obviously hinder a rapid and complete healing of the skin.

In the use of the above and of other possible remedies against burns, a timely application is extremely important. It may be anticipated that the therapy will be the more effective the shorter is the time elapsed between the event that caused the lesions and the application of the remedy on the said lesions. Suitable products may be in the form of ointments or salves, creams, emulsions, gels, foams, sprays or medicated dressings or bandages, which must be directly applied on the affected zone and must be kept into contact with the lesion, if necessary by soaking the dressing from the exterior with further product, until the reparative process is seen to stably proceed.

In the past, skin burns have been covered with dressings such as salves, vaseline, and fibrous or synthetic polymer bandages, in an effort to prevent dehydration, protect against heat loss, prevent bacterial infection, and to maintain a moist environment about the wound to facilitate debridement. Conventional bandages are made of materials such as natural or synthetic fibers. One problem with such conventional covers is that, as the skin exudes serum and pus, this exudate is absorbed by the bandage. This proteinaceous material provides a culture medium for bacteria. Further, as the exudate hardens, the bandage is likely to become adhered to the skin. As the bandage is removed, the scab is also frequently removed. This can be extremely painful.

Various compounds have been developed as an alternative to, or for use with, bandages. For example, U.S. Pat. No. 85,385 (Hughes) teaches a medicinal compound suitable for treatment of skin ailments including burns, which composition is made by mixing and simmering cider-vinegar, molasses, spirits of turpentine, salt, saltpeter, oil of vitriol, and olive oil.

U.S. Pat. No. 321,839 (Neuer) teaches a medicinal compound for treatment of skin wounds, comprising thymol, boracic acid, potassium chloride, sodium chloride, and oil of wintergreen.

U.S. Pat. No. 390,534 (Tomlinson) teaches a lotion for treatment of sores, wounds and the like, comprising water, gambier extract, salt, and sulphuric acid.

Exemplary of these is U.S. Pat. No. 4,732,755 (Grana), which teaches the application of sodium polyacrylate powder as a dressing over the skin burn area, and wetting the powder such as by spraying with distilled water, until the powder becomes moist. The outer wetted surface of the moistened powder dries to form a parchment like surface, and may remain in place for 2–3 weeks.

U.S. Pat. No. 4,837,019 (Georgalas et al.) teaches a skin treatment composition for treating burned skin, which composition is capable of counteracting moisture loss and promote healing, and which comprises a moisturizing component formed of polyglycerylmethacrylate, glycerine, allantoin, panthenol, amino acid complex, and fibronectin.

U.S. Pat. No. 5,009,890 (DiPippo) discloses a burn treatment product in the form of a water-soluble, biodegradable gel, the active ingredients of which are water and Tea Tree Blend. A gum material is used to maintain the water and Tea Tree Blend in a gel state.

A number of compositions have been developed for the treatment of skin burns, but these compositions contain medications, which are expensive and not readily available.

In each case discussed above, the composition is either expensive or is formulated from ingredients which is not readily available or is not found to be entirely effective. Further, the application of various of the prior art compositions to a burn may require medical training and constant attention. Further, various patients may have reactions to certain of the non-naturally occurring pharmaceutical compositions.

In view of the foregoing, it is an object of the present invention to provide a topical composition for treatment of skin burns which eliminates or minimizes the above-mentioned and other problems, limitations and disadvantages typically associated with conventional topical compositions, and to provide a topical composition which is inexpensive, easily obtainable, simple to manufacture, easy to apply and use, reliable, storage-stable, and which does not necessarily require medical professional to administer.

SUMMARY OF THE INVENTION

In accordance with the invention, there is provided, a topical composition for treatment of burns of the skin consisting essentially of a mixture of olive oil, bees wax, lemon juice, and boric acid, wherein the amounts of olive oil and bees wax are such that the mixture is essentially a cream or thick liquid.

In accordance with the invention there is provided a topical composition for the treatment of burns of the skin, essentially of a mixture of olive oil, bees wax, lemon juice, and boric acid, wherein the amounts of olive oil and bees wax are such that the mixture is essentially a cream or thick liquid wherein the parts by weight ratio of olive oil to bees wax to lemon juice to boric acid are within 50% of 200 to 60 to 40 to 6 respectively, and wherein the ratio of olive oil to bees wax is such that the composition is a cream or liquid After extensive investigation and experimentation, the present inventor has discovered that the objects of the invention can be simply, eloquently, and inexpensively accomplished by a topical composition for the treatment of burns comprising a mixture of, olive oil, beeswax, lemon juice and boric acid.

Testing was done by treating burns with different combinations of the above-mentioned ingredients and the results were unexpected. Using boric acid ($H_3BO_3$) alone appeared to advance healing without infection but only in a very limited fashion. Combining boric acid with lemon juice alone did not promote healing in a much more significant way. The use of beeswax mixed with olive oil alone also appeared to advance healing as olive oil is known as known as a demulcent, emollient and soothing to mucous membranes and somewhat effective for burns, bruises, insect bites, sprains and intense itching, however the combination of all four ingredients produced significantly most improved results with the fastest healing with the least amount of scarring.

DETAILED DESCRIPTION OF THE INVENTION

The present invention more specifically concerns a topical composition and method for treatment of traumatized skin, i.e., thermal burns ranging from mild injury to extensive necrosis of the skin and/or underlying tissues. The composition and method not only expedites the healing of first and second degree burns, which are normally capable of healing without scarring, but also promotes the healing of third degree burns without scar tissue.

The ability to heal third degree burns without scarring is important not only for the treatment of accidental burns, but also in the treatment of intentional burns, such as thermal burns for destruction of birthmarks, disfiguring scars resulting from earlier injury, and the like.

The composition of the present invention is capable of application to mammals in general and humans in particular.

This invention is particularly useful when applied to traumatized tissue immediately after injury, but may also be applied one or more days after injury. Healing begins promptly upon application of the composition to the affected area, and the duration of healing will vary, depending upon the extent of the injury, from a few days to a few weeks.

EXAMPLES

In the following example a composition was prepared by mixing approximately by weight 200 grams of olive oil, 60 grams of bees wax, 40 grams of lemon juice and 6 grams of boric acid. There is no particular restriction on the manner of mixing, and common kitchen implements can be used. The composition was applied to a thickness of about ¼ of an inch evenly. For $2^{nd}$ and $3^{rd}$ degree burns the composition was applied more thickly and was and wrapped with gauze. In all instances optimum results were achieved re-applying three times daily.

Preferably, 40–60% of the composition by weight is olive oil, and 12–25% is beeswax. Notwithstanding, the amount of beeswax should be limited the desired consistency which varies from a thick paste to a more dilute cream or liquid. Lemon juice by weight may range from 5–20% and boric acid by weight comprises less than 10%. In yet a more preferred embodiment, the percentage by weight of olive oil, bees wax, lemon juice, and boric acid is, 60–70%, 16–24%, 10–16% and 1–6% respectively.

In applications where gauze was used, gauze with a fresh amount of cream was used to carefully remove any dead skin after which the a layer of the composition and new gauze was re-applied.

Ensuring that dead skin is removed between applications promoted the best healing with the least scarring.

Example 1

A female in her early 40's was severely burned from boiling liquid over the top of her right hand. Unfortunately this subject had no knowledge of the composition in accordance with this invention, and used ice water and ice packs with sterile gauze padding. Four days later her right hand was very red, painful and unsightly. She started applying the composition of this invention and relief was immediate. It was applied three times a day and the following morning was much less sensitive to touch. To her surprise, four days after applying the cream the burn had healed with no blisters forming, pustules or scarring.

Numerous other patients were treated for first, second and third degree burns with astonishing success. In all instances the surprising results with the instant relief to the pain that was associated with the burn and the lack of or reduced amount of scarring normally associated with such burns.

The composition is made in the following manner.

Approximately 200 grams of olive oil is heated and the 60 grams of hard bees wax is added until it softens, then 6 grams of boric acid is added and the mixture is removed from the heat source. 40 grams of lemon is then added.

It should be understood that the aforementioned amounts by weight are preferable, however, different amounts of these ingredients provide some benefit. What must be taken into account is the required consistency. For example if too much bees wax or too little olive oil is added, the mixture will be too hard to use. Alternatively, more, or less lemon juice can be used with relatively useful results.

The topical composition consists essentially of a mixture of olive oil, bees wax, lemon juice, and boric acid, wherein the amounts of olive oil and bees wax are such that the mixture is essentially a cream or a thick liquid, and wherein the total amounts by weight of olive oil and bees wax to boric acid is at least 10:1. Preferably the parts by weight ratio of olive oil to bees wax to lemon juice to boric acid are within 50% of: 200 to 60 to 40 to 6 respectively.

It is preferred that by weight, more olive oil is present than bees wax; more bees wax is present than lemon juice; and, more lemon juice is present than boric acid.

A preferred range of the constituents by weight is:

olive oil is 40–70%; beeswax is 12–25%; lemon juice is 12–25%; and, boric acid is 0.5–6%.

Yet a more preferred range which has shown to yield optimum results, by weight is: olive oil 60–70% beeswax 16–24% lemon juice 10–16% boric acid 1–6%.

Although olive oil yields excellent results, other oils with similar properties may be substituted.

Numerous other embodiments may be envisaged, without departing from the sprit and scope of the invention.

What is claimed is:

1. A topical composition for the treatment of bums of the skin consisting essentially of:
   olive oil, bees wax, lemon juice, and boric acid, wherein the total amounts by weight of olive oil and bees wax to boric acid is at least 10:1.

2. A topical composition as defined in claim 1, wherein at least 80% of said composition consists of olive oil, bees wax, lemon juice and boric acid.

3. A topical composition as defined in claim 2, wherein by weight:
   more olive oil is present than bees wax;
   more bees wax is present than lemon juice; and,
   more lemon juice is present than boric acid.

4. A topical composition as defined in claim 3 wherein the lemon juice by weight is between 5–20%.

5. A topical composition for treatment of bums of the skin as defined in claim 3 wherein olive oil is present 60–70% by weight, bees wax is present 16–24% by weight lemon juice is present 10–16% by weight, and boric acid is present 1–6% by weight.

6. A topical composition as defined in claim 1, wherein:
   the percentage by weight of said olive oil is 40–70%;
   the percentage by weight of said beeswax is 12–25%;
   the percentage by weight of said lemon juice is 12–25%; and,
   the percentage by weight of said boric acid is 0.5–6%.

7. A topical composition for treatment of bums of the skin consisting essentially of a mixture of olive oil, bees wax, lemon juice, and boric acid, wherein the amounts of olive oil and bees wax are such that the mixture is essentially a cream or a thick liquid, and wherein the total amounts by weight of olive oil and bees wax to boric acid is at least 10:1.

8. A topical composition for the treatment of burns of the skin as defined in claim 1 wherein the parts by weight ratio of olive oil to bees wax to lemon juice to boric acid are within (100–300) to (30–90) to (20–60) to (3–9), respectively.

9. A method of preparing the composition as defined in claim 7, comprising the steps of:
   heating the olive oil and bees wax and mixing to form a mixture;
   adding and mixing the boric acid into the mixture;
   adding and mixing the lemon juice into the mixture; and,
   allowing the mixture to cool.

* * * * *